(12) United States Patent
Patrini et al.

(10) Patent No.: US 6,218,583 B1
(45) Date of Patent: Apr. 17, 2001

(54) PROCESS FOR THE PRODUCTION OF ETHERS FROM ALCOHOLS

(75) Inventors: Renata Patrini; Mario Marchionna, both of Milan (IT)

(73) Assignee: Snamprogetti S.p.A., S. Donato Milanese (IT)

( * ) Notice: Subject to any disclaimer, the term of this patent is extended or adjusted under 35 U.S.C. 154(b) by 0 days.

(21) Appl. No.: 09/045,904

(22) Filed: Mar. 23, 1998

(30) Foreign Application Priority Data

Apr. 2, 1997 (IT) .............................................. MI97A0754

(51) Int. Cl.⁷ .................................................... C07C 41/09
(52) U.S. Cl. .............................................................. 568/698
(58) Field of Search ............................................... 508/698

(56) References Cited

U.S. PATENT DOCUMENTS

| | | | |
|---|---|---|---|
| 1,868,076 | * 7/1932 | Richard | 568/698 |
| 1,961,987 | * 6/1934 | Schumann et al. | 568/698 |
| 2,430,388 | * 11/1947 | Carnell | 568/698 |
| 2,443,906 | * 6/1948 | Guinot et al. | 568/698 |
| 5,689,014 | * 11/1997 | Frey et al. | 568/698 |

FOREIGN PATENT DOCUMENTS

| | | |
|---|---|---|
| 41 27 230 | 2/1993 | (DE) . |
| 44 38 581 | 5/1996 | (DE) . |
| 195 11 668 | 10/1996 | (DE) . |
| 195 17 049 | 11/1996 | (DE) . |
| 243736 | 7/1926 | (GB) . |
| WO 92/13819 | 8/1992 | (WO) . |

* cited by examiner

*Primary Examiner*—James H. Reamer
(74) *Attorney, Agent, or Firm*—Oblon, Spivak, McClelland, Maier & Neustadt, P.C.

(57) ABSTRACT

Process for the production of ethers starting from alcohols, in the presence of liquid acid catalysts, essentially comprising the following steps:

Figure 1:
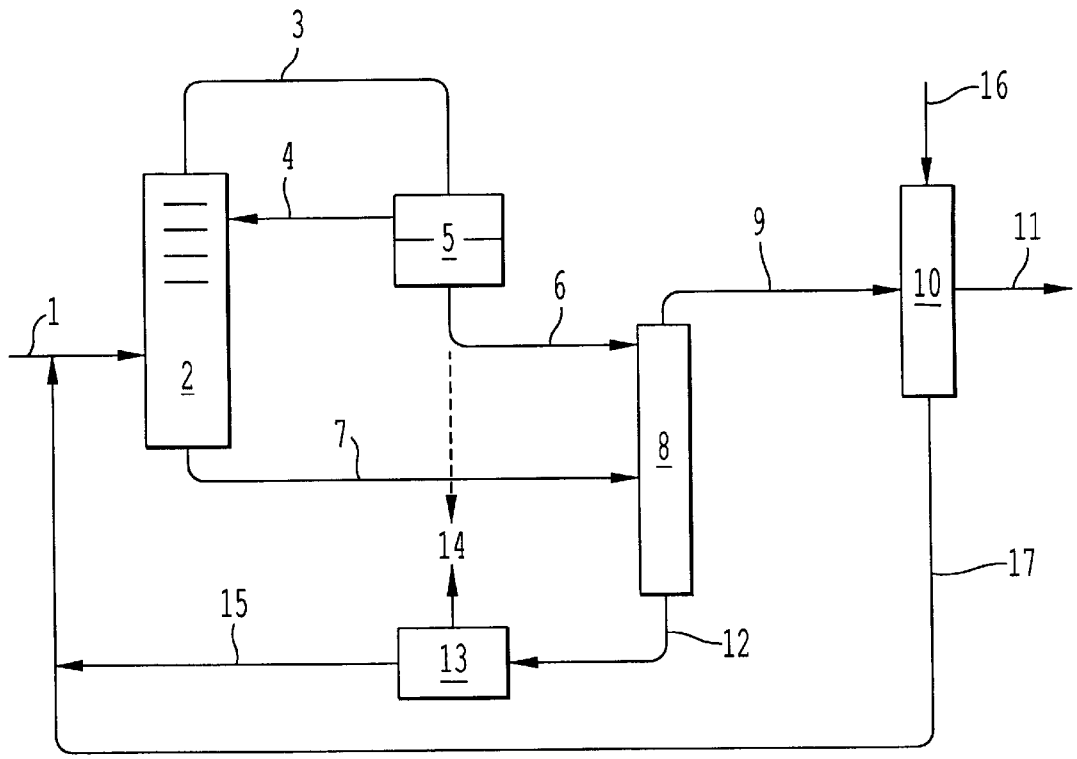

a) sending a stream containing $C_4$–$C_{10}$ alcohols to a reaction zone obtaining a product essentially consisting of ethers and the acid catalyst;

b) feeding the product essentially consisting of ethers and the acid catalyst to an extraction zone with $C_4$–$C_{10}$ alcohols in order to obtain a stream essentially consisting of ethers and a stream containing said alcohols and said catalyst;

c) sending the non-reacted alcohols and the water formed by the reaction zone to a distillation zone from which an azeotropic alcohol/water stream is obtained together with the residual stream which is sent to the reaction zone;

d) sending the azeotropic alcohol/water stream to a separation zone to separate the alcohol, which is recycled to the reaction zone, from the aqueous stream.

14 Claims, 1 Drawing Sheet

PROCESS FOR THE PRODUCTION OF ETHERS FROM ALCOHOLS

The present invention relates to a process for the selective production of ethers from alcohols with the use of liquid acid catalysts and more specifically the production of di-alkyl ethers from the corresponding alcohols.

Di-alkyl ethers form, among other things, interesting products with a high cetane number which can contribute to the formulation of diesel gasoils with better performances and reduced emissions.

Whereas various process alternatives are available for improving the quality of gasolines, as far as gas oil is concerned, which is a notably less developed product than gasoline, there seem to be two main ways of obtaining a good quality refinery product: either the crude oil is of a high quality, and the gas oil obtained by distillation is therefore of an excellent quality (necessitating only quite a bland hydrotreatment) or recourse must be made to forced hydrotreatment and Hydrocracking processes on the various fractions.

A third solution is to synthesize, or obtain from other sources, synthetic fuels or fuels of a natural origin which can form high-quality components for reformulated gas oils: examples of the first category are Fischer-Tropsch gas oils (by means of the SMDS process; Tijm P. J. A., ACS August (1994), 1146) and an example of the second category is "bio-diesel" deriving from seed oils (Staat F., Valley E., Chemistry & Industry (1994) 863).

Another particularly interesting group of compounds consists of linear ethers, with a total number of atoms of ≧9, which have a blending cetane number which is more than double the specific value of present gas oils and with extremely advantageous properties at cold temperatures (Pecci G. C., Clerici M. G., Giavazzi F., Ancillotti F., Marchionna M., Patrini R., IX Int. Symp. Alcohols Fuels, (1991), 1, 321; Giavazzi F., Terna D., Patrini R., Ancillotti F., Pecci G. C., Trere R., Benelli M., IX Int. Symp. Alcohols Fuels, (1991)1,327).

In Europe the future specifications on fuel seem to be directed towards diesel with an ever increasing cetane number (especially if regulations are introduced for regulating cold emissions), at the same time reducing the content of sulfur and polyaromatic hydrocarbons.

As linear ethers radically improve the cetane number and properties at cold, they therefore represent very promising additives from the point of view of performance and environment (Marchionna M., Patrini R., Giavazzi F., Pecci G. C., Preprints 212th Nat. Meet. Am. Chem. Soc., Div. Petr. Chem, (1996),41, 585).

In addition to this possible use, alkyl ethers already have a wide variety of industrial uses such as both reaction and extraction solvents, and are also widely applied in the fields of dyes, paints, rubbers, resins and lubricants.

Ethers are generally produced by means of three main synthesis groups:
a) Williamson Synthesis
RX+R'ONa→R'OR+NaX (X=Br, I, . . . )
b) Sum of alcohol based on alkene
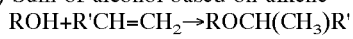
ROH+R'CH=CH$_2$→ROCH(CH$_3$)R'
c) Dehydration of alcohol (bimolecular)
2ROH→ROR+H$_2$O Reactions b) and c) both take place with acid catalysis and are the most widely used syntheses in industrial applications; the sum b) of alcohol with olefin is only possible when the double olefin bond is substituted so as to give a secondary or tertiary carbocation and has found great industrial development for the synthesis of MTBE, ETBE and TAME, all additives with a high octane number for gasoline.

The bimolecular dehydration reaction c) of alcohol on the other hand is particularly useful for obtaining symmetrical ethers from primary alcohols, even if it can also be advantageously used for secondary alcohols; in the latter case it is difficult however to obtain high selectivities to ethers with respect to the olefinic by-product, obtained by monomolecular dehydration

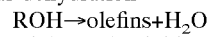
ROH→olefins+H$_2$O

Higher selectivities have recently been obtained, in the case of secondary alcohols, by the use of suitable reactors and catalysts (Brown S. H., U.S. Pat. No. 5,444,168, (1995)).

In addition the olefins produced can subsequently be added to the alcohol to give branched ethers with a different structure from the ether produced by bimolecular dehydration; therefore if high selectivities into the above ether are desired, it is necessary to reduce the production of olefins to the minimum.

So far in industrial practice the dehydration of alcohols has been catalyzed with sulfuric acid; this catalyst generally offers quite high selectivities to ether (>80–85%) but has various problems: it is generally used in high concentrations, it is corrosive and in addition, whereas the selectivity to olefins is rather low, heavy products are generally formed (alkyl sulfates, etc.) which tend to blacken the product and complicate the recovery of the acid catalyst.

To overcome these problems, the use of acid cationic resins was proposed in the past (Karpov O. N., Bystrova R. M., Fedoysuk L. G., Zh. Prikl. Khim., 40(1967)219); these catalysts are quite active and selective (yields to di-n-pentylether, DNPE, of about 80% starting from n-pentanol) but there are considerable problems of stability at the reaction temperature: with alcohols and ethers with a boiling point of >120° C. (from n-butanol to higher products), the catalyst is rapidly deactivated.

It is known that also other acid catalysts of the sulfonic type (toluene-sulfonic, fluoro-sulfonic, triflic, etc.) are used in this type of reaction. Their use has also been cited in recent patents but little information has been given on their performance and above all there is no information on the separation and recycling process of the catalyst (Bohlander R., Ridinger R., DE-4438581, (1996); Daute P., Fies, M., DE-19511668, (1996)); in some cases the acid is neutralized by means of treatment with a base.

It has now been found that by operating with a particular process using liquid acid catalysts and using an apparatus for the azeotropic removal of the water (mixed with the alcohol) from the reaction environment, almost total yields to ethers are obtained starting from the corresponding alcohols, also allowing a simple and functional recovery of the catalyst from the reaction product and its recycling to the reaction environment.

The process of the present invention for the production of ethers starting from the corresponding alcohols, in the presence of liquid acid catalysts, essentially comprises the following steps:
a) sending a stream containing C$_4$–C$_{10}$ alcohols to a reaction zone obtaining a product essentially consisting of ethers and the acid catalyst;
b) feeding the product essentially consisting of ethers and the acid catalyst to an extraction zone with C$_4$–C$_{10}$ alcohols in order to obtain a stream essentially consisting of ethers and a stream containing said alcohols and said catalyst;
c) sending the non-reacted alcohols and the water formed by the reaction zone to a distillation zone from which an azeotropic alcohol/water stream is obtained together with the residual stream which is sent to the reaction zone;

d) sending the azeotropic alcohol/water stream to a separation zone to separate the alcohol, which is recycled to the reaction zone, from the aqueous stream.

The product consisting of the ethers and acid catalyst, before being sent to the extraction zone (b), is optionally sent to a further extraction zone in which at least part of the aqueous stream separated in (d) is fed in countercurrent.

The $C_4$–$C_{10}$ alcohols used are alicyclic primary alcohols and can contain cyclic and aromatic groups; aliphatic alcohols however are those particularly preferred.

The alcohols used can also be mixed with each other.

In fact the process claimed is particularly suitable when streams are used coming from hydroformylation processes which contain n-butanol and 2-methylpropanol and/or n-pentanol and 2-methyl-butanol:

When only one aliphatic alcohol is subjected to reaction, symmetrical dialkylethers are obtained with a high selectivity; when, on the other hand mixtures of aliphatic alcohols are treated, mixed ethers are also obtained.

A wide variety of liquid acid catalysts can be used for this process; among these, for example, mineral acids such as sulfuric acid and substituted sulfonic acids, Lewis acids ($BF_3$), phosphoric acid, can be mentioned. Among these catalysts the use of perfluoroalkanesulfonic acids such as triflic acid or higher derivatives, such as for example perfluorobutanesulfonic acid, are the most preferred.

A wide range of operating conditions can be used for producing alkyl ethers in the desired selectivities using the process claimed herein. It is possible to operate in liquid phase or in liquid-vapor phase but the operating conditions in liquid-vapor phase are preferred. Particularly preferred is a reactor configuration which allows the separation in continuous of the water produced by the formation of the azeotropic alcohol/water mixture which vaporizes in the reaction environment; after cooling the azeotropic mixture, the water and alcohol are separated, the latter then being passed to the reaction environment.

The process of the present invention can operate both under batch and continuous conditions, the latter however being more advantageous in industrial practice. The reactor configuration can optionally be selected from an isothermal, adiabatic, stirred reactor; a column reactor which contemporaneously allows the separation of the products can also be used for the purposes of the present invention, even if it is generally sufficient to use a less costly apparatus such as a typical reactor with an overlying plate column which favours the removal of the water with the method described above.

The range of process conditions, operating in liquid or liquid-vapor phase, comprises a wide variety of operating conditions listed hereunder.

The reaction temperature can be within the range of 50 to 300° C., preferably between 120 and 280° C., more preferably the boiling point of the alcohol-ether mixture, thus varying between the boiling point of the alcohol and that of the ether, whereas the pressure can vary from 0.1 to 1 MPa.

An alcohol-ether stream can also be fed into the reaction if the reaction temperature is to be maintained high.

The molar ratio alcohol/acid is generally greater than 5, preferably greater than 25.

The reaction is preferably carried out with an almost total conversion of the alcohol also to facilitate the recovery of the catalyst; it is understood however that small percentages of non-reacted alcohol can be separated at the head from the reaction products by distillation, together with the olefins produced by intramolecular dehydration.

As mentioned above, the ether product containing the catalyst can be sent to a washing column with water which extracts the acid catalyst and is then definitely purified from the catalyst and traces of water by treatment with columns containing silica gel; in this case a completely deacidified product can be obtained without the use of bases which, on neutralizing the acid, produce salts which are difficult to dispose of.

Other materials with typical absorbing properties can be used but the use of silica is considered preferable for its low cost and ideal absorption and desorption capacity.

The aqueous solution containing the acid can be suitably concentrated to partly eliminate the excess water and then recycled together with fresh alcohol into the reaction environment; the acid absorbed by the silica gel on the other hand can be easily extracted by elution with fresh alcohol and the mixture of alcohol and acid obtained can be recycled together with the other streams to the reactor.

Operating in this way the loss of catalyst is practically zero; in addition, the activity of the catalyst in these passages remains unaltered.

In another configuration, again already mentioned, the ether stream containing the catalyst can be sent directly to the columns containing silica gel (obviously with different dimensions from the previous case owing to the increased volume of acid to be recovered) and is then treated as in the previous case.

The extraction columns can be either in series or parallel and can operate both in absorption phase to purify the ether and elution phase to recycle the acid to the reactor.

The concentration of the perfluoroalkanesulfonic acid can vary within a wide range depending on the specific requirements and alcohol in the reaction; however it is preferably between 0.0005 and 1 M.

An illustrative diagram of the process is shown in FIG. 1; similar schemes can also be prepared for alcohols in mixture.

The alcohol stream (1), containing the alcohol and optionally the fresh catalyst, is sent to a reactor (2) (preferably enamelled to avoid corrosion phenomena) where the reaction takes place in the lower part, whereas in the upper part, where the distillation plates are situated, an azeotropic alcohol/water stream (3) is extracted, which is then cooled and sent to a decanter (5) in which the alcohol (4) is separated and recycled to the reactor. The aqueous stream (6) is on the other hand, either separated or sent for water storage (14), or sent countercurrent to an extraction column (8) of the mixture of ether and catalyst (7) leaving the reactor (2).

The aqueous stream (12) containing almost all of the catalyst, leaving the extraction column (8), is sent to a concentrator (13) to eliminate part of the water (14) which is added to the stream coming from (5). The concentrated acid stream (15) is recycled to the reactor (2) together with stream (1).

The ether stream (9) leaving the column (8) is sent to a set of columns (10) filled with silica gel where the ether is purified of the last traces of water and acid and is sent for storage (11). The latter components can be re-extracted with fresh alcohol (16) and recycled to the reactor (17) together with the concentrated acid stream (15).

Figure 2:
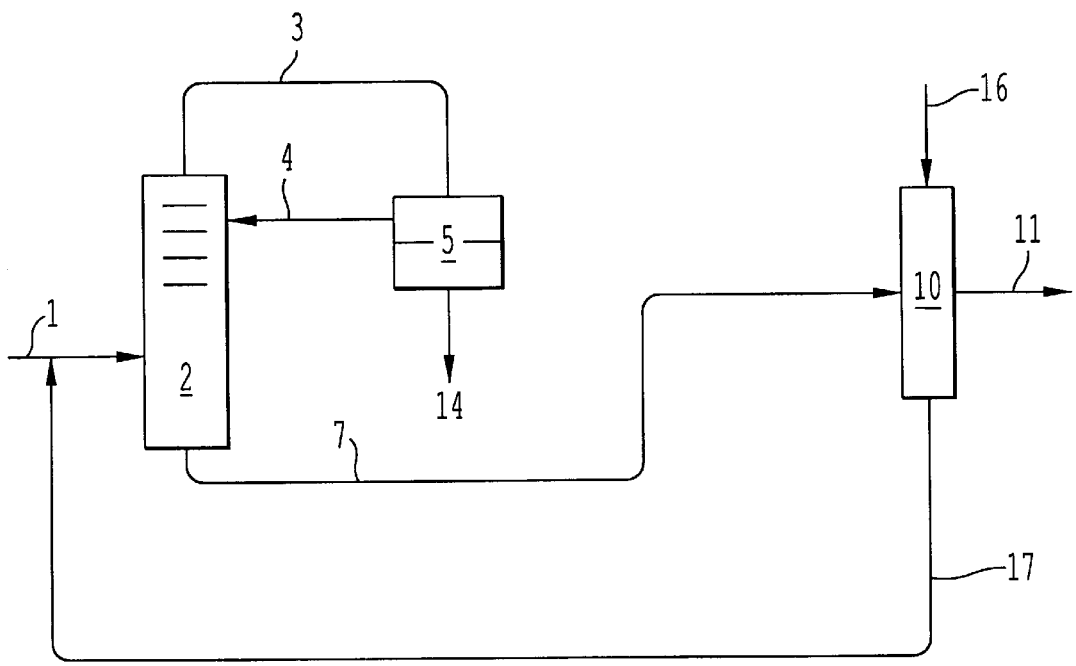

The second option is shown in FIG. 2; in this case the mixture of ether and catalyst (7) leaving the etherification reactor (2) is sent directly to the set of columns (10) filled with silica gel where the ether (11) is purified of all the acid and traces of water. The latter components can be eluted with fresh alcohol (16) and recycled to the reactor (17).

The following examples provide a better illustration of the present invention but in no way limit its scope.

EXAMPLES

Reactors were used consisting of flasks with a capacity of between 250 and 1500 ml equipped with a thermocouple holder for the continuous registration of the reaction temperature and a Dean-Stark apparatus with a reflux condenser for removing the water formed and thus favouring the equilibrium towards the formation of ether; the head of the condenser is connected to a trap cooled with dry ice for condensing the lighter olefins; the flasks are heated by complete immersion in thermostat-regulated oil-baths.

The tests were carried out at reflux; they are considered complete when the content of water corresponding to the theoretical stoichiometrical quantity produced by the reaction has been collected in the Dean-Stark; the reaction temperature then tends to become stable.

Example 1

In this test n-pentanol (500 ml, 4.6 moles) was used as primary alcohol in the presence of 7.5 ml (83.8 mmoles) of triflic acid ($CF_3SO_3H$).

Operating under the conditions described above (bath thermostat-regulated at 160° C.) it was possible to obtain after 510 minutes of reaction a conversion of n-pentanol of 93.6%, with a production of 37.8 ml of $H_2O$ and with a selectivity to di-n-pentylether (DNPE) of 93.67%. The by-products consisted of pentenes (3.98%), $C_6$–$C_{10}$ compounds (0.24%), mixed ethers containing branched structures (1.85%) and heavy products, $C_{15}^+$, (0.26%); the data are shown in Table I.

The initial temperature in the reactor was 136° C., and the final temperature 151° C.

The colour of the end-product containing the catalyst is yellowish.

It was subjected to three washings with $H_2O$ (total 3×15 ml); the ether extracted contained 0.10 mmoles of $H^+$ (titrated for acidimetric analysis). The ether stream was percolated on a column containing 28 ml of activated silica gel 70.200 mesh for 2 h at 200° C.; an acid-base titration showed that after the treatment the product no longer contained acid.

The ether product became completely colourless whereas the silica became a light yellow.

Other DNPE fractions containing acid were passed over the same silica until 2.5 mmoles of $H^+$ had been absorbed.

The acid remaining on the column can be completely eluted with 50 ml of n-pentanol; after treatment with alcohol the silica gel is completely colourless.

Example 2

This example shows how the recycled catalyst (after treatment with water) is active and has an even better selectivity than the fresh catalyst.

The stream coming from the aqueous washing described in the previous experiment is used. The results are shown in Table I.

The end-product after extraction and treatment on silica gel is colourless.

Example 3 (Comparative)

In this test n-pentanol (100 ml, 0.92 moles) was used as primary alcohol in the presence of sulfuric acid ($ROH/H^+$= 8.5). operating under the conditions described above it was possible to obtain after 240 minutes of reaction a conversion of n-pentanol of 82%, with a production of 8.3 ml of $H_2O$ and with a selectivity to di-n-pentylether (DNPE) of 82.6%. The by-products consisted of pentenes (8.5%), $C_6$–$C_{10}$ compounds (0.9%), mixed ethers containing branched structures (1.1%) and heavy products, $C_{15}^+$, (6.9%).

The initial temperature in the reactor was 130° C., and the final temperature 156° C.

The colour of the solution containing the product and catalyst is dark yellow (brown).

Examples 4–11

Table II shows the data relating to test carried out in sequence; in each test (n-pentanol 100 ml) the catalyst extracted from the previous test was used. These examples show that the catalyst can be easily recycled without any loss in activity and selectivity.

Examples 12–13

Table III shows the data relating to tests carried out with n-pentanol (100 ml); in example 13, 50 ml of di-n-pentyl-ether (DNPE) were also added and there were reductions in the duration of the reaction.

Examples 14–16

Table IV indicates tests carried out with n-pentanol (500 ml) and varying quantities of catalyst in a bath at a constant temperature of 160° C.

The results show that the reaction rate depends on the concentration of the catalyst, whereas the best selectivities are obtained at lower concentrations of catalyst.

Examples 17–20

Table V indicates tests carried out with mixtures of alcohols (n-pentanol - 2-methyl-butanol) 500 ml total, under the same operating conditions.

Examples 21–22

Table VI indicates tests carried out with n-pentanol (500 ml) and in a bath at a constant temperature of 160° C. in example 21 and at a constant temperature of 180° C. in example 22.

The results show that the reaction rate depends on the reaction temperature.

Examples 23–24

Direct treatment with silica

In example 23, 250 ml of n-pentanol (2.3 moles) were etherified in the presence of 0.9 ml (10.3 mmoles) of triflic acid ($CF_3SO_3H$), operating under the conditions described above; results are shown in table VII.

The reaction product containing ether and triflic acid was percolated on a column containing 28 ml of silica gel 70.200 mesh; an acid-base titration on the percolated product shows that after the treatment the product no longer contains acid and is completely colourless whereas the silica becomes light yellow.

The acid absorbed by the silica gel was eluted (example 24) with 250 ml of pentanol and the solution obtained, containing acid and alcohol, subjected to etherification (Table VII).

TABLE I

| Ex. | CF$_3$SO$_3$H (mmol) | ROH/H$^+$ | T (° C.) | TIME (min.) | Conver. (%) | C$_5$ | C$_{6-10}$ | Select. (%) ROR' | ROR | C$_{15}^+$ |
|---|---|---|---|---|---|---|---|---|---|---|
| 1 | 83.8 | 54.5 | 137–151 | 510 | 93.6 | 3.98 | 0.24 | 1.85 | 93.67 | 0.26 |
| 2 | extract. | 54.5 | 137–151 | 480 | 93.5 | 3.26 | 0.20 | 1.81 | 94.46 | 0.27 |

TABLE II

| Ex. | CF$_3$SO$_3$H (mmol) | ROH/H$^+$ | T (° C.) | TIME (min.) | Conver. (%) | C$_5$ | C$_{6-10}$ | Select. (%) ROR' | ROR | C$_{15}^+$ |
|---|---|---|---|---|---|---|---|---|---|---|
| 4 | 17.1 | 54.5 | 137–157 | 560 | 91.8 | 0.8 | 0.05 | 2.2 | 96.9 | 0.05 |
| 5 | extract. | 54.5 | 137–157 | 520 | 96.0 | 2.6 | 0.1 | 1.5 | 95.7 | 0.1 |
| 6 | extract. | 54.5 | 137–157 | 390 | 91.1 | 0.6 | 0.1 | 1.4 | 97.7 | 0.2 |
| 7 | extract. | 54.5 | 137–157 | 385 | 96.0 | 0.8 | 0.05 | 1.3 | 97.8 | 0.05 |
| 8 | extract. | 54.5 | 137–157 | 295 | 94.1 | 0.8 | 0.1 | 1.1 | 97.9 | 0.1 |
| 9 | extract. | 54.5 | 137–157 | 415 | 95.1 | 0.7 | 0.05 | 1.3 | 97.9 | 0.05 |
| 10 | extract. | 54.5 | 137–157 | 445 | 95.0 | 1.0 | 0.05 | 1.3 | 97.6 | 0.05 |
| 11 | extract. | 54.5 | 137–157 | 420 | 95.3 | 1.1 | 0.05 | 1.3 | 97.5 | 0.05 |

TABLE III

| Ex. | CF$_3$SO$_3$H (mmol) | ROH/H$^+$ | T (° C.) | TIME (min.) | Conver. (%) | C$_5$ | C$_{6-10}$ | Select. (%) ROR' | ROR | C$_{15}^+$ |
|---|---|---|---|---|---|---|---|---|---|---|
| 12 | 17.07 | 54 | 137–151 | 360 | 96.0 | 1.4 | 0.1 | 0.7 | 97.7 | 0.1 |
| 13 | 17.07 | 54 | 137–151 | 320 | 96.5 | 1.9 | 0.1 | 1.3 | 96.6 | 0.1 |

TABLE IV

| Ex. | CF$_3$SO$_3$H (mmol) | ROH/H$^+$ | T (° C.) | TIME (min.) | Conver. (%) | C$_5$ | C$_{6-10}$ | Select. (%) ROR' | ROR | C$_{15}^+$ |
|---|---|---|---|---|---|---|---|---|---|---|
| 14 | 170.1 | 26.9 | 137–148 | 280 | 91.4 | 6.3 | 0.55 | 2.2 | 90.7 | 0.25 |
| 15 | 83.8 | 54.5 | 137–151 | 510 | 93.6 | 4.0 | 0.2 | 1.8 | 93.7 | 0.3 |
| 16 | 19.9 | 230.3 | 137–152 | 1510 | 90.5 | 0.7 | 0.05 | 1.6 | 97.6 | 0.05 |

TABLE V

| Ex. | CF$_3$SO$_3$H (mmol) | ROH/ 2MeBuOH | T (° C.) | TIME (min.) | Conver. (%) n PEOH | Conver. (%) 2MeBuOH | C$_5$ | C$_{6-10}$ | Select. (%) ROR' | ROR | C$_{15}^+$ |
|---|---|---|---|---|---|---|---|---|---|---|---|
| 17 | 54.5 | 100–0 | 137–151 | 510 | 93.6 |  | 4.0 | 0.2 | 1.8 | 93.7 | 0.3 |
| 18 | 54.5 | 95–5 | 137–151 | 570 | 95.7 | 87.6 | 2.6 | 0.1 | 9.5 | 87.5 | 0.3 |
| 19 | 54.5 | 90–10 | 137–151 | 575 | 95.9 | 95.8 | 3.8 | 0.3 | 17.4 | 78.3 | 0.2 |
| 20 | 54.5 | 85–15 | 137–151 | 645 | 96.7 | 97.2 | 6.7 | 0.9 | 22.7 | 68.9 | 0.8 |

TABLE VI

| Ex. | CF$_3$SO$_3$H (mmol) | ROH/H$^+$ | T (° C.) | TIME (min.) | Conver. (%) | C$_5$ | C$_{6-10}$ | Select. (%) ROR' | ROR | C$_{15}^+$ |
|---|---|---|---|---|---|---|---|---|---|---|
| 21 | 19.9 | 230.3 | 137–151 | 1510 | 90.5 | 0.7 | 0.05 | 1.6 | 97.6 | 0.05 |
| 22 | 19.9 | 230.3 | 137–169 | 1260 | 94.1 | 1.55 | 0.05 | 1.7 | 96.6 | 0.1 |

TABLE VII

| Ex. | $CF_3SO_3H$ (mmol) | $ROH/H^+$ | T (° C.) | TIME (min.) | Conver. (%) | $C_5$ | $C_{6-10}$ | Select. (%) ROR' | ROR | $C_{15}^+$ |
|---|---|---|---|---|---|---|---|---|---|---|
| 23 | 10.3 | 230 | 137–179 | 1150 | 93 | 1.6 | 0.1 | 1.7 | 96.5 | 0.1 |
| 24 | recov. | 230 | 137–179 | 1020 | 93 | 1.8 | 0.1 | 1.4 | 96.6 | 0.1 |

What is claimed is:

1. A process for the production of ethers starting from corresponding alcohols comprising:

a) reacting a stream comprising $C_{4-10}$ alcohols in the presence of a liquid acid catalyst in a reaction zone, to obtain a product comprising ethers, said liquid acid catalyst, said $C_{4-10}$ alcohols and water;

b) removing said $C_{4-10}$ alcohols and said water by azeotropic distillation from said product in a distillation zone, to produce a stream comprising said ether and said liquid acid catalyst and a stream comprising said $C_{4-10}$ alcohols and said water;

c) extracting said liquid acid catalyst with $C_{4-10}$ alcohols in an extraction zone, from said stream comprising said ether and said liquid acid catalyst; and d) separating said $C_{4-10}$ alcohols in a separation zone, from said stream comprising said $C_{4-10}$ alcohols and said water, and recycling said $C_{4-10}$ alcohols to said reaction zone.

2. The process according to claim 1 wherein the product consisting of ethers and the acid catalyst, before being sent to the extraction zone (c), is sent to an additional extraction zone in which at least part of the aqueous stream separated in (d) is fed in countercurrent.

3. The process according to claim 1 wherein the liquid acid catalysts are perfluoroalkanesulfonic acids.

4. The process according to claim 3 wherein the perfluoroalkanesulfonic acids are selected from triflic acid and higher derivatives thereof.

5. The process according to claim 1 wherein the concentration of the liquid acid catalyst is between 0.0005 and 1 M.

6. The process according to claim 1 wherein the reaction is carried out at a temperature of between 50 and 300° C. and at a pressure of between 0.1 and 1 MPa.

7. The process according to claim 6 wherein the reaction is carried out at a temperature of between 120 and 280° C.

8. The process according to claim 7 wherein the reaction is carried out at the boiling point of the alcohol-ether mixture.

9. The process according to claim 1 wherein the molar ratio alcohols/liquid acids is greater than 5.

10. The process according to claim 9 wherein the molar ratio alcohols/liquid acids is greater than 25.

11. The process according to claim 1 wherein an alcohol-ether stream is sent to the reaction zone.

12. The process according to claim 1 wherein the $C_4$–$C_{10}$ alcohols are selected from primary alcohols.

13. The process according to claim 12 wherein the primary alcohols are aliphatic.

14. The process according to claim 1 wherein the $C_4$–$C_{10}$ alcohols are mixtures of n-butanol and 2-methylpropanol or n-pentanol and 2-methyl-butanol.

* * * * *